(12) United States Patent
Hudson

(10) Patent No.: US 6,673,257 B1
(45) Date of Patent: Jan. 6, 2004

(54) THERMAL CUTOFF CONSTRUCTION COMPOSITIONS

(75) Inventor: Christine M. Hudson, Hudson, OH (US)

(73) Assignee: Therm-O-Disc, Incorporated, Mansfield, OH (US)

( * ) Notice: Subject to any disclaimer, the term of this patent is extended or adjusted under 35 U.S.C. 154(b) by 265 days.

(21) Appl. No.: 09/659,981

(22) Filed: Sep. 12, 2000

(51) Int. Cl.$^7$ ............... C04B 35/00; C07D 307/89; C07C 45/27; C07C 69/76; C07F 9/00
(52) U.S. Cl. ............... 252/62.3 Q; 252/183.11; 252/510; 252/511; 252/519.3; 549/249; 552/208; 552/261; 556/42; 556/45; 556/57; 560/76
(58) Field of Search ............... 552/208, 261; 549/249; 560/76; 252/183.11, 510, 511, 519.3, 519.32, 62.3 Q; 556/42, 45, 57

(56) References Cited

U.S. PATENT DOCUMENTS 4,514,718 A     4/1985   Birx

FOREIGN PATENT DOCUMENTS

DE           186526      *  2/1904

OTHER PUBLICATIONS

Parker, Modern Plastics, 36(10), 135–136, 138, 208 (1959).*
Aldrich Catalog p. 42, 114,606, 1181 (1996).*

* cited by examiner

Primary Examiner—Johann Richter
Assistant Examiner—Sikarl A. Witherspoon
(74) Attorney, Agent, or Firm—Harness, Dickey & Pierce, P.L.C.

(57) ABSTRACT

A thermal cutoff member and compositions used to manufacture such members are described herein as including at least two organic compounds which, when sufficiently combined, give rise to a component which has a lower melt transition temperature than the initial organic compounds prior to combining the same. The thermal cutoff member is generally utilized in a thermal cutoff construction having an electrical switching unit that changes its operating condition when the member therein melts by being heated to a certain temperature for the particular material that forms the member being utilized.

26 Claims, 1 Drawing Sheet

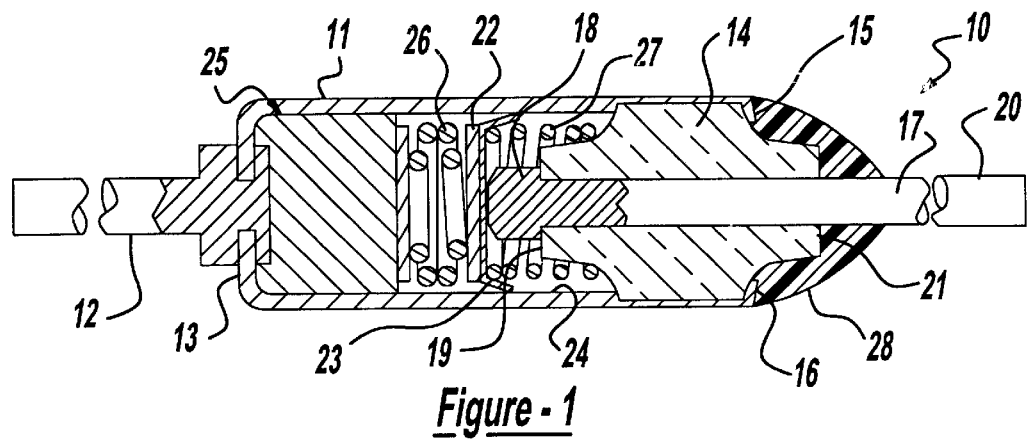
*Figure - 1*
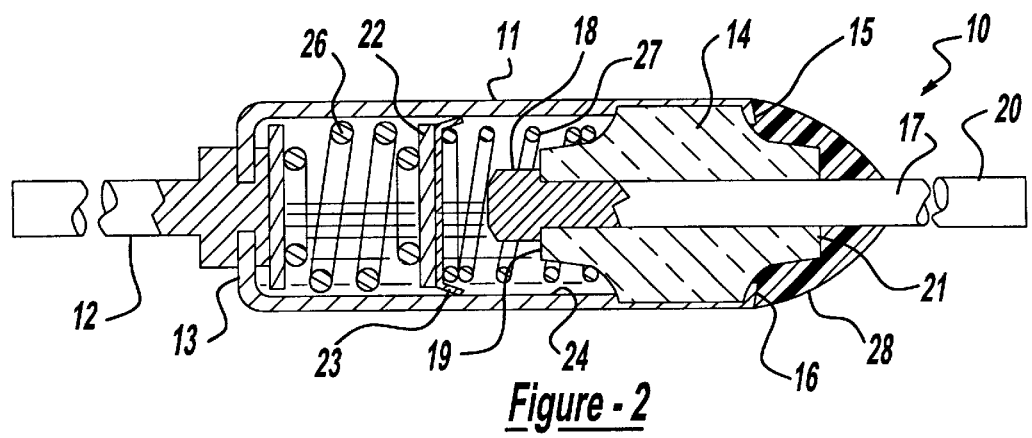
*Figure - 2*
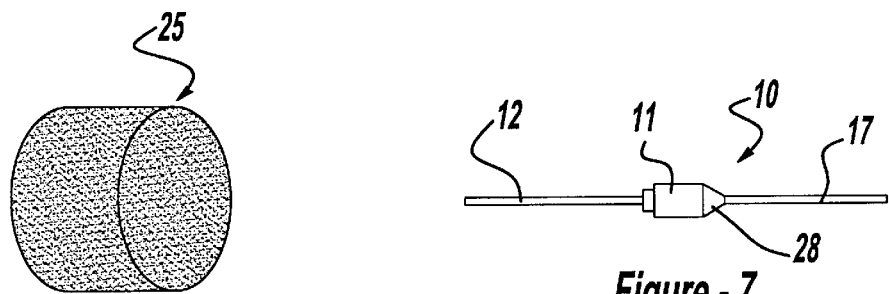
*Figure - 3*
*Figure - 7*
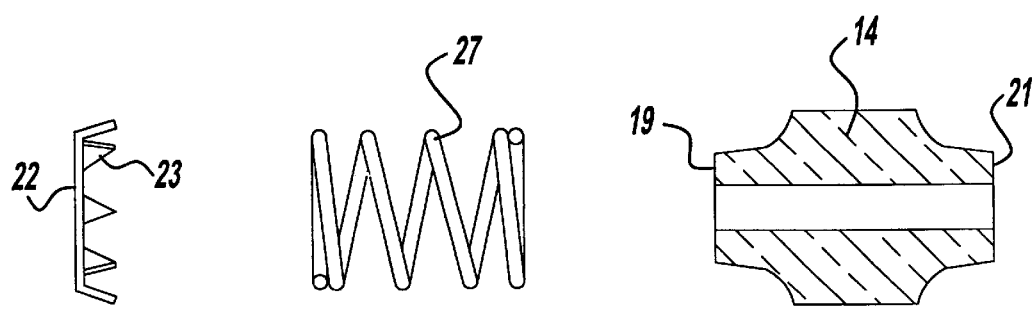
*Figure - 4*   *Figure - 5*   *Figure - 6*

THERMAL CUTOFF CONSTRUCTION COMPOSITIONS

BACKGROUND OF THE INVENTION

1. Field of the Invention

This invention relates to compositions useful for cutoff devices and, more particularly, the thermal cutoff compositions employing a mixture of at least two crystalline organic compounds.

2. Background of the Invention

It is known to provide thermal cutoff assemblies having electrical switching units which change its operating condition when a member disposed therein melts by being heated to a certain temperature. The members typically include what will hereinafter be referred to as a thermal cutoff composition.

Heretofore, thermal cutoff compositions have been formulated from a single organic compound having a known melting temperature commonly in pellet form. These compounds were typically blended with a binder, such as an epoxy, a lubricant such as calcium stearate and/or a pigment such as a metal oxide for purposes of color coding the pellet. For example, U.S. Pat. No. 4,514,718 discloses 4-methylumbelliferone as a preferred organic compound for thermal cutoff applications. While the foregoing thermal cutoff composition has proven useful, significant improvements and advantages are provided by the present invention.

As will be understood by those skilled in the art, the melt temperature is not the only characteristic of thermal cutoff compositions which is important. In addition, the composition should be chemically stable, thermally stable and typically electrically non-conductive in the molten state.

SUMMARY OF THE INVENTION

It is a feature of this invention to provide thermal cutoff compositions useful in association with thermal cutoff constructions wherein the composition is capable of being formed into a member adapted to melt (or otherwise changes shape) at a certain temperature or other condition and thereby cause an electrical switching unit of the thermal cutoff construction to change its operating condition.

In particular, it has been found that blends employing at least two organic compounds having known melt temperatures, when brought together via blending or otherwise combined, exhibit improved thermal properties and performance characteristics over the individual organic components. In addition to having the desired melt temperatures, the compositions of the present invention exhibit good chemical and thermal stability. Further, the thermal cutoff compositions are electrically non-conductive in the molten state.

For purposes of the present invention, it is important to note that the phrase "melting point temperature" as used herein, does not refer to a temperature wherein the product is at the equilibrium point between liquid and solid phases. Rather, melting point temperature is to be considered the temperature at which the thermal cutoff composition (pellet) no longer possesses the structural integrity required to maintain a switch in a held open or held closed position depending on the embodiment. To the extent that such melt temperatures require measurement, various apparatuses such as those produced by Thomas Hoover, Mettler and Fisher-Johns may be employed. Differential Scanning Colorimetry (DSC) techniques are also useful.

Accordingly, it is a primary object of this invention to provide thermal cutoff compositions for forming members employed in thermal cutoff constructions.

It is a further object of the present invention to provide thermal cutoff compositions with defined melt temperature ranges.

Other objects, uses and advantages of this invention should be apparent from a reading of the detailed description, particularly when taken in conjunction with the accompanying drawings wherein:

BRIEF DESCRIPTION OF THE DRAWINGS

FIG. 1 is an enlarged cross sectional view of a thermal cutoff construction utilizing the member of this invention;

FIG. 2 is a view similar to FIG. 1 and illustrates the thermal cutoff construction after the actuating member thereof has melted to cause the electrical switching unit thereof to change its operating condition;

FIG. 3 is a side perspective view illustrating the improved actuating member of this invention;

FIG. 4 is a side view of a sliding contact member of the switch construction of FIG. 1;

FIG. 5 is a side view of one of the springs of the switch construction of FIG. 1;

FIG. 6 is a cross sectional view of the ceramic end plug of the switch construction of FIG. 1;

FIG. 7 is an elevation view of the thermal cutoff construction of FIG. 1, but in reduced size illustrating approximately the actual size of the thermal cutoff construction.

DETAILED DESCRIPTION OF THE PREFERRED EMBODIMENTS

While several features of this invention are described and illustrated in this specification, and this invention can be adapted to provide thermal cutoff compositions to be used in thermal cutoff constructions, it is to be understood that the various disclosed features of this invention are not exhaustive; further, such features can be utilized singly or in any combination thereof to provide such a member of different configurations and/or for other types of thermal cutoff constructions as desired.

Therefore, this invention is not to be limited to only the embodiment illustrated in the drawings because the drawings are merely utilized to illustrate one of the wide variety of uses of the thermal cutoff compositions. For example and without limitation, the thermal cutoff compositions of the present invention would generally be useful in association with the entire MICROTEMP® line of thermal cutoff assemblies commercially available by Therm-O-Disc, Inc. of Mansfield, Ohio.

Referring now to FIGS. 1, 2 and 7, the thermal cutoff construction that utilizes the improved features of this invention is generally indicated by the reference numeral 10 and is substantially identical to the thermal limiter construction disclosed in U.S. Pat. No. 4,075,595 to Plasko; U.S. Pat. No. 3,180,958 to Merrill; U.S. Pat. No. 3,519,972 to Merrill, and, in particular, U.S. Pat. No. 4,514,718 to Birx, whereby these four U.S. patents are incorporated into this disclosure by this reference thereto for any information desired as to the details of the particular parts and operation of the thermal cutoff construction 10. As such, the thermal cutoff construction 10 will merely be described in a general manner.

In general, the thermal cutoff construction 10 includes a conductive metallic casing 11 having a metallic electrical conductor 12 secured in electrical contact with a closed end 13 of the casing 11. A ceramic end plug 14, as best illustrated in FIG. 6, is disposed in an open end 15 of the casing 11 and is secured thereto by a turned over portion 16 of the end 15 of the casing 11 as illustrated in FIG. 1 while being sealed thereto by an epoxy seal 28, a second metallic electrical conductor 17 passing through the bushing 14 and having an enlarged head 18 disposed against one end 19 of the end plug 14 and another end 20 projecting out of the outer end 21 of the end plug 14 and seal 28 for external lead attachment purposes.

A sliding conductive contact member 22 of metallic material, as best illustrated in FIG. 4, is disposed inside the casing 11 and has resilient peripheral fingers 23 disposed in sliding engagement with the internal peripheral surface 24 of the casing 11 to provide electrical contact therebetween.

A thermally responsive pellet-like member 25, as best illustrated in FIG. 3, is formed of material in a manner hereinafter set forth and is disposed in the casing 11 against the end wall 13 thereof.

A pair of compression springs 26 and 27 are respectively disposed on opposite sides of the sliding contact member 22 such that the compression spring 26 is in a compressed condition between the solid member 25 and the contact member 22 and has a stronger compressed force than the force of the compressed spring 27 which is disposed between the contact member 22 and the end plug 14 whereby the contact member 22 is held by the force of the spring 26 in electrical contact with the enlarged end 18 of the conductor 17 so that an electrical circuit is provided between the conductors 12 and 17 through the casing 11 and sliding contact member 22 of the thermal cutoff construction 10 as illustrated in FIG. 1.

However, when the particular temperature for melting the pellet-like member 25 is reached, such as during an adverse heating condition adjacent the thermal cutoff construction 10, the member 25 melts in the manner illustrated in FIG. 2 whereby the springs 26 and 27 are adapted to expand, as illustrated by spring 27 in FIG. 5, and thereby through the relationship of the particular forces and length of the springs 26 and 27, the sliding contact member 22 is moved out of electrical contact with the end 18 of the second conductor 17 in the manner illustrated in FIG. 2 so that the electrical circuit between the conductors 12 and 17 through the thermal cutoff construction 10 is broken and remains open as illustrated in FIG. 2.

The improved thermal cutoff compositions of the present invention comprise at least two distinct thermally and chemically stable organic compounds which, when combined, exhibit improved properties, such as a melting point temperature lower than either of the starting compounds while remaining electrically non-conductive in the molten state. By "electrically non-conductive", it is preferably meant that the composition is capable of withstanding a 240 volt, 60 Hz sinusoidal potential between two electrodes at least 5° C. above the melt transition temperature, for one minute without conducting greater than 250 mA. More preferably, the composition should be capable of withstanding a 240 volt, 60 Hz sinusoidal potential at least 10° C. above the melt transition temperature for at least about one minute without conducting greater than 250 mA. Under highly preferred embodiments, the thermal cutoff compositions of the present invention should be capable of withstanding a 240 volt, 60 Hz sinusoidal potential at least 60° C. above the melt transition temperature for at least about one minute without conducting greater than 250 mA.

While the thermal cutoff compositions of the present invention should meet or exceed the aforementioned test protocol, it should be understood by those skilled in the art that the compositions are contemplated as being useful for both low voltage and high voltage applications. Further, the compositions of the present invention are expected to meet or exceed UL1020 or EN 60 691 standards.

Preferably, the resulting thermal cutoff composition will have a melting point temperature of between about 60° C. to 300° C. and, more preferably, between about 65° C. to about 265° C. Under a highly preferred embodiment the resulting composition will be non-deliquescent, i.e., moisture repellant. As noted above, once intimately combined, the resulting component has a lower melting point temperature than any of the individual organic compounds employed. The differential in melting point temperatures of the organic compounds (pre-blend) versus the thermal cutoff composition (post-blend) gives rise to a composition having a depressed melting point of at least 5° C. That is, the resulting thermal cutoff composition will have a melting point temperature as the term is used herein of at least 5° C. lower than any of the individual organic compounds employed. The depressed melting point of at least 5° C. should result regardless whether the compounds are blended, co-precipitated, co-crystallized or otherwise intimately combined.

By way of non-limiting example, the organic compounds set forth in Table I below are considered useful in formulating the thermal cutoff compositions of the present invention. Each of the below listed organic compounds are crystalline in nature and have melting point temperatures of between about 60° C. to about 300° C.

TABLE I

| Name | CAS Registry No. | Melt Point Range*(° C.) | Molecular Weight (g/mole) |
|---|---|---|---|
| 2H-1-benzopyran-2-one | 91-64-5 | 68–70 | 146 |
| n-butyl-4-hydroxybenzoate | 94-26-8 | 68–69 | 194 |
| phenylbenzoate | 93-99-2 | 69–72 | 198 |
| diphenyl phthalate | 84-62-8 | 74–76 | 318 |
| 4-hydroxy-3-methoxybenzaldehyde | 121-33-5 | 81–83 | 152 |
| 1,3-diphenylbenzene | 92-06-8 | 84–88 | 230 |
| 1,4-dibromobenzene | 106-37-6 | 87–89 | 235 |
| triphenylmethane | 519-73-3 | 92–94 | 244 |
| 4,4'methylene bis (benzeneamine) | 101-77-9 | 89–91 | 198 |
| diphenylethanedione | 134-81-6 | 94–95 | 210 |
| pentanedioic acid | 110-94-1 | 95–98 | 132 |
| n-propyl-4-hydroxybenzoate | 94-13-3 | 95–98 | 180 |
| xanthene | 92-83-1 | 101–102 | 188 |
| 3,5-dimethylpyrazole | 67-51-6 | 107–109 | 96 |
| 1,3-benzenediol | 108-46-3 | 110–113 | 110 |
| N-phenyl-2-napthylamine | 135-88-6 | 107–109 | 219 |
| N-phenylacetamide | 103-84-4 | 113–115 | 135 |
| 9H-fluorene | 86-73-7 | 114–116 | 166 |
| m-phenylenedibenzoate | 94-01-9 | 117 | 318 |
| dihydro-2,5-furandione | 108-30-5 | 119–120 | 100 |
| 2,,5-pyrrolidinedione | 123-56-8 | 123–125 | 99 |
| 3-pyridinecarboxamide | 98-92-0 | 130–132 | 122 |
| phthalic anhydride | 85-44-9 | 131–134 | 148 |
| p-toluenesulfonamide | 70-55-3 | 138–139 | 171 |
| dimethyl terephthalate | 120-61-6 | 140–142 | 194 |
| N-(4-methylphenyl)acetamide | 103-89-9 | 149–151 | 149 |
| hexanedioic acid | 124-04-9 | 152–154 | 146 |
| N-phenylbenzamide | 93-98-1 | 164–166 | 197 |
| 4,4'-dibromobiphenyl | 92-86-4 | 167–170 | 312 |
| mannitol | 69-65-8 | 167–170 | 182 |
| 4-(1,1-dimethylethyl)benzoic acid | 98-73-7 | 165–167 | 178 |
| N-(2,6-dimethylphenyl)acetamide | 2198-53-0 | 182–184 | 163 |
| 2,4-dinitrobenzeneamine | 606-22-4 | 137–139 | 183 |
| 7-hydroxy-4-methylcoumarin | 90-33-5 | 190–190 | 176 |
| 5,5-diethyl-2,4,6(1H,3H,5H)-pyrimidinetrione | 57-44-3 | 189–191 | 184 |

TABLE I-continued

| Name | CAS Registry No. | Melt Point Range*(° C.) | Molecular Weight (g/mole) |
|---|---|---|---|
| 1,4-diphenylbenzene | 92-94-4 | 212–213 | 230 |
| inositol | 87-89-8 | 224–225 | 180 |
| 6-phenyl-1,3,5-triazine-2,4-diamine | 91-76-9 | 226–228 | 187 |
| 2-phenylbenzimidazole | 716-79-0 | 293–296 | 194 |
| 3,7-dihydro-1,3,7-trimethyl-1H-purine-2,6-dione | 58-08-2 | 232–236 | 194 |
| 1,1'-bi-2-naphthol | 602-09-5 | 214–217 | 286 |
| 4-hydroxy-3-methoxybenzoic acid | 121-34-6 | 209–213 | 168 |
| 2,3-dimethylanthraquinone | 6531-35-7 | 210–212 | 236 |
| 2-phenylindole | 948-65-2 | 188–190 | 193 |
| 2-methylphenylacetic acid | 644-36-0 | 88–90 | 150 |
| 1,3,5-trimethyl-2,4,6tris(3,5-di-tertbutyl-4-hydroxybenzyl)benzene | 1709-70-2 | 248–250 | 774 |
| hydantoin | 461-72-3 | 221–223 | 100 |
| 7-hydroxycoumarin | 93-35-6 | 230 | 162 |
| Carbanilide | 102-07-8 | 239–241 | 212 |
| 1,5-dichloroanthraquinone | 82-46-2 | 245–247 | 277 |
| 1,1,1-tris(4-hydroxyphenyl)ethane | 27955-94-8 | 246–248 | 306 |
| 1-Aminoanthraquinone | 82-45-1 | 253–255 | 223 |
| 2,3,5,6-tetrabromo-p-xylene | 23488-38-2 | 254–256 | 422 |
| 1,5-dihydroxynapthalene | 83-56-7 | 259–261 | 160 |
| 2-quinoxalinol | 1198-57-2 | 271–272 | 146 |
| 2,4-diamino-6-methyl-1,3,5-triazine | 542-02-9 | 274–276 | 125 |
| 7-chloro-4-hydroxyquinoline | 86-99-7 | 276–279 | 180 |
| Alizarin | 72-48-0 | 279–284 | 240 |
| Anthraquinone | 84-65-1 | 284–286 | 208 |
| 2,4-diamino-6-hydroxypyrimidine | 56-06-4 | 285–286 | 126 |
| 2-phenylbenzimidazole | 716-79-0 | 296–296 | 194 |
| 2-amino-4-hydroxy-6-methylpyrimidine | 3977-29-5 | >300 | 125 |
| 4-amino-2,6-dihydroxypyrimidine | 873-83-6 | >300 | 127 |
| 2-amino-4,6-dihydroxypyrimidine | 56-09-7 | >300 | 127 |
| Uracil | 66-22-8 | >300 | 112 |

In addition to the above described at least two organic compounds, the thermal cutoff compositions of the present invention may optionally include a binder component. The binder, which generally softens (melts) at a temperature below the melting point of the crystalline component, is primarily utilized to assist in the production of pellets. While various binders known for pellet formation can be utilized, preferred binders include polyethylene glycol, 1,3-benzenediol, epoxies, polyamides and mixtures thereof. The binder is generally present in amounts up to about 10.0 wt. % based on the total composition.

Additionally, it may be desirable to employ a lubricant to enforce the flow and fill properties when processing pellets. For example, among the numerous lubricants which have proven useful are calcium stearate, boron nitride, magnesium silicate and polytetrafluoroethylene (teflon), among others. The lubricant is generally present in amounts of up to about 5.0 wt. % based on the total composition.

It may also be desirable under certain applications to incorporate coloring agents such as pigments into the thermal cutoff composition to allow for rapid visual inspection of the pellets condition. Virtually any known pigment which is compatible with the aforementioned thermal cutoff composition components may be employed. Pigments, when employed, are typically present in amounts of up to about 2.0 wt. %.

To analyze the effectiveness of the thermal cutoff compositions of the present invention, various samples as set forth in Table II were prepared and tested to determine the target thermal cutoff temperature range, while exhibiting other desirable characteristics.

TABLE II

| CAS Reg. No. | 58-08-2 | 91-78-9 | 92-94-4 | 90-33-5 | 2198-53-0 | 93-98-1 | 103-89-9 | 120-61-6 | 123-58-8 |
|---|---|---|---|---|---|---|---|---|---|
| 58-08-2 | xxx | | | | | | | | |
| 91-78-9 | 177.8(8.9) | xxx | | | | | | | |
| 92-94-4 | 187.78(−11.7) | 201.1(−16.9) | xxx | | | | | | |
| 90-33-5 | 145.6(19.6) | 169.9(2.9) | 181.4(−15.0) | xxx | | | | | |
| 2198-53-0 | two peaks @−164.2 | 169.6(−7.8) | 169.1(−14.9) | 137.6(11.0) | xxx | | | | |
| 93-98-1 | 143.5(1.1) | 158.9(−5.8) | 156.2(−8.4) | 142.5(1.6) | 131.4(−2.8) | xxx | | | |
| 103-89-9 | 137.0(−2.6) | 145.5(3.0) | 144.5(−6.7) | 126.3 (premelt) | 120.0(0.7) | 122.4(−1.2) | xxx | | |
| 120-81-6 | 131.3(−2.6) | 136.9(−1.2) | 134.5(−2.5) | 134.8(−4.5) | 131.8(−14.6) | 124.9(−4.8) | 121.7 (−8.7) | xxx | |
| 123-58-8 | 111.6(−2.2) | 120.1(−0.4) | multi peak | 115.6(−1.6) | 114.6(−14.7) | 114.0(−11.8) | 107.4(−10.2) | 116.2(−20.4) | xxx |
| 94-01-9 | 110.8(0.1) | *116.6(−0.7) | 113.7(0.1) | *115.5(−2.3) | 112.8(−9.6) | 109.5(−3.0) | 107.3(−4.2) | 101.4(0.5) | 108.5(−21.6) |
| 103-84-4 | 107.2(2.0) | *113.7(−1.7) | 113.3(−4.1) | 101.4(7.2) | 95.2(0.2) | 100.1(0.2) | 99.0(−2.6) | 102.2(−6.8) | 88.2(−10.8) |
| 67-51-6 | 102.7(−7.7) | mult. peak | mult. peak | mult. peak | 95.6(−11.8) | mult. peak | 87.9(−1.3) | 97.0(−11.2) | 82.9(−18.5) |
| 92-83-1 | | 98.3(0.5) | *101.3 | 99.2(−13.1) | 97.8(−8.8) | 97.3(−9.2) | 89.3(−1.8) | mult peak | |
| 134-81-6 | | *93.1(−0.7) | *94.4 | 91.6(−9.2) | 89.5(−2.45) | 89.3(−4.9) | 85.5(−1.5) | 90.2(−21.7) | |
| 519-73-3 | | *91.5(−0.9) | *93.6 | 92.7(−12.6) | *91.6(6.6) | *91.9(−9.5) | 85.9(−3.9) | mult. peak | |
| 108-37-6 | | 84.7(0.6) | *87.8 | *86.3(−11.2) | mult. peak | *85.7(−8.0) | 79.9(−2.4) | mult. peak | |
| 121-33-5 | | multi. peak | *80.2 | 74.9(−3.5) | 77.1(−1.0) | 72.3(1.7) | 75.8(−1.9) | 64.9(−5) | |
| 84-62-8 | | *74.0(0.6) | | *72.8(−5.7) | *72.6(−1.9) | *72.5(−3.5) | 71.1(−1.9) | *72.4(−15) | |

TABLE II-continued

| CAS Reg. No. | 94-01-9 | 103-84-4 | 67-51-6 | 92-83-1 | 134-81-6 | 519-73-3 | 106-37-6 | 121-35-5 | 84-62-8 |
|---|---|---|---|---|---|---|---|---|---|
| 58-08-2 | | | | | | | | | |
| 91-78-9 | | | | | | | | | |
| 92-94-4 | | | | | | | | | |
| 90-33-5 | | | | | | | | | |
| 2198-53-0 | | | | | | | | | |
| 93-98-1 | | | | | | | | | |
| 103-89-9 | | | | | | | | | |
| 120-81-6 | | | | | | | | | |
| 123-58-8 | | | | | | | | | |
| 94-01-9 | xxx | | | | | | | | |
| 103-84-4 | 95.2(−7.3) | xxx | | | | | | | |
| 67-51-6 | 92.2(−13.4) | 74.6(−5.8) | xxx | | | | | | |
| 92-83-1 | 80.9(0.7) | 89.8(−16.2) | 82.2(−19.4) | xxx | | | | | |
| 134-81-6 | 77.9(1.1) | 80.4(−8.8) | 77.7(−18.9) | 68.5(−1.9) | xxx | | | | |
| 519-73-3 | 81.1(−4.0) | 89.0(−19.5) | 80.7(21.9) | 65.8(−1.5) | 66.1(−2.93) | xxx | | | |
| 108-37-6 | 73.3(−.02) | 81.3(−16.1) | 72.0(−17.4) | 60.0(0.4) | 62.7(−2.3) | 57.2(0) | xxx | | |
| 121-33-5 | 74.1(−3.9) | 62.5(0.3) | mult. peak | 71.2(−12.8) | 64.5(−6.9) | 73.9(−18.4) | 67.1(−15.0) | xxx | |
| 84-62-8 | 68.4(−1.8) | 87.4(−8.7) | 67.1(−14.9) | 59.7(−2.8) | 57.0(−0.5) | 80.0(−5.4) | 56.1(−1.4) | 58.9(−8.4) | xxx |

*No change from starting material
Numbers in ( ) represent Predicted $T_a$-Experimental $T_a$ Once it is determined that each of the listed compounds, when mixed with a second compound, give rise to viable thermal cutoff compositions, certain samples may be prepared to verify whether compounds may be formulated with specific cutoff target temperatures.

Initially, a first sample can be prepared with the objective of obtaining a product having an expected melting point temperature (melt transition temperature) of about 176° C. The sample can be prepared by mixing between about 38% to about 60% by weight 3,7-dihydro-1,3,7-trimethyl-1H-purine-2,6-dione with 62% to about 40% by weight 1,4-diphenylbenzene in a high speed grinding mill mixer. Added to the aforementioned organic compounds may be 1% by weight of a polyamide binder and 1% by weight of an organic azo pigment. The resulting composition is expected to exhibit a melting point temperature of about 188° C.

Additional samples can be prepared with the objective of obtaining a product having a melting point temperature of about 162° C. In this regard, a sample can be prepared by mixing a three compound blend including 45% by weight 1,1'-bi-2-naphthol, 19.5% by weight 6-phenyl-1,3,5-triazine-2,4-diamine and 35.5% by weight 3,7-dihydro-1,3,7-trimethyl-1H-purine-2,6-dione in a high speed grinding mill mixer. After blended for approximately five minutes, the sample may be analyzed using differential scanning calorimetry (DSC). The resulting composition is expected to exhibit a melting point temperature of about 154° C.

A third sample can be prepared with the objective of obtaining a product having a melting point temperature of about 108° C. The samples are prepared by mixing 14–16% by weight 7-hydroxy-4-methylcoumarin with N-phenylacetamide in a high speed grinding mill mixer. After blending for approximately five minutes, the sample may be analyzed using differential scanning calorimetry (DSC). The resulting composition is expected to exhibit a melting point temperatures of about 102° C.

A fourth sample can be prepared with the objective of achieving a composition having a melting point temperature of about 74° C. The sample can be prepared by mixing 14–16% by weight of N-(4-methylphenyl) acetamide with 84–86% by weight 4-hydroxy-3-methoxybenzaldehyde in a high speed grinding mill mixer. After blended for approximately five minutes, the sample may be analyzed using differential scanning calorimetry (DSC). The resulting composition is expected to exhibit a melting point temperature of about 72° C.

In addition to exhibiting repeatable transition melt temperatures, the compositions of the present invention are also expected to exhibit clean current interrupt properties, decreased composition costs and should allow for designing thermal cutoffs to specific customer needs. Further, the compositions of the present invention can be quantitatively analyzed using known techniques such as proton or carbon nuclear magnetic resonance, mass spectroscopy or Fourier transform infrared spectroscopy techniques, by way of non-limiting example.

As demonstrated by the foregoing samples, thermal cutoff compositions of the present invention may be custom formulated to give precise thermal cutoff temperatures, while exhibiting other important characteristics such as chemical and thermal stability. While the thermal cutoff composition may be formed into the shape such as that illustrated in FIG. 3, it should be understood that the material can be formed in other shapes and still provide its actuating function at the target melting temperatures.

While it will be apparent that the preferred embodiments of the invention disclosed are well calculated to fulfill the objects stated, it will be appreciated that the invention is susceptible to modification, variation and change without departing from the spirit thereof.

What is claimed is:

1. A thermal cutoff composition comprising:

at least two crystalline organic compounds, said compounds having a melting point temperature of less than about 300° C. with the difference in melting point temperature of at least two organic compounds employed being not more than about 100° C.; and at least one component selected from the group consisting of binders, lubricants and coloring agents;

wherein, the resulting thermal cutoff composition has a melting point temperature which is less than that of any of the individual organic compounds prior to being combined.

2. The thermal cutoff composition of claim 1 wherein said at least two organic compounds are selected from the group consisting of:

2H-1-benzopyran-2-one; n-butyl-4-hydroxybenzoate; phenylbenzoate; diphenylphthalate; 4-hydroxy-3-methoxybenzaldehyde; 1,3-diphenylbenzene; 1,4-dibromobenzene; triphenylmethane; 4,4'methylene bis (benzeneamine); diphenylethanedione; pentanedioic acid; n-propyl-4-hydroxybenzoate; xanthene; 3,5-dimethylpyrazole; 1,3-benzenediol; N-phenyl-2-napthylamine; N-phenylacetamide; 9H-fluorene; m-phenylenedibenzoate; dihydro-2,5-furandione; 2,5-pyrrolidinedione; 3-pyridinecarboxamide; phthalic anhydride; p-toluenesulfonamide; dimethyl terephthalate; N-(4-methylphenyl)acetamide; hexanedioic acid; N-phenylbenzamide; 4,4'-dibromobiphenyl; mannitol; 4-(1,1-dimethylethyl)benzoic acid; N-(2,6-dimethylphenyl)acetamide; 2,4-dinitrobenzeneamine; 7-hydroxy-4-methylcoumarin; 5,5-diethyl-2,4,6(IH,3H,5H)-pyrimidinetrione; 1,4-diphenylbenzene, inositol; 6-phenyl-1,3,5-triazine-2,4-diamine; 3,7-dihydro-1,3,7-trimethyl-1H-purine-2,6-dione; 1,1'-bi-2-naphthol; 4-hydroxy-3-methoxybenzoic acid; 2,3-dimethylanthraquinone; 2-phenylindole; 2-methylphenylacetic acid; 2-phenylbenzimidazole, 1,3,5-trimethyl-2,4,6tris(3,5-di-tertbutyl-4-hydroxybenzyl)benzene; hydantoin; 7-hydroxycoumarin; carbanilide; 1,5-dichloroanthraquinone; 1,1,1-tris(4-hydroxyphenyl) ethane; 1-aminoanthraquinone; 2,3,5,6-tetrabromo-p-xylene; 1,5-dihydroxynapthalene; 2-quinoxalinol; 2,4-diamino-6-methyl-1,3,5-triazine; 7-chloro-4-hydroxyquinoline; alizarin; anthraquinone; 2,4-diamino-6-hydroxypyrimidine; 2-phenylbenzimidazole; 2-amino-4-hydroxy-6-methylpyrimidine; 4-amino-2,6-dihydroxypyrimidine; 2-amino-4,6-dihydroxypyrimidine and uracil.

3. The thermal cutoff composition of claim 1 wherein said composition is electrically non-conductive.

4. The thermal cutoff composition of claim 3 wherein said composition is capable of withstanding a 240 volt, 60 Hz sinusoidal potential between electrical conductors at least 5° C. above the melt transition temperature for at least about one minute without conducting greater than 250 mA.

5. The thermal cutoff composition of claim 3 wherein said composition is capable of withstanding a 240 volt, 60 Hz sinusoidal potential between electrical conductors at least 60° C. above the melt transition temperature for at least about one minute without conducting greater than 250 mA.

6. The thermal cutoff composition of claim 1 comprising a binder selected from the group consisting of polyethylene glycol, 1,3-benzenediol, epoxies, and polyamides.

7. The thermal cutoff composition of claim 1 wherein said composition is pelletized.

8. The thermal cutoff composition of claim 1 wherein said composition is non-deliquescent.

9. The thermal cutoff composition of claim 1 wherein said composition has a depressed melting point of at least 5° C.

10. A thermal cutoff composition made by a process comprising the steps of:

combining at least two crystalline organic compounds together with at least one component selected from the group consisting of binder, lubricant, and pigment, said compounds having a melting point temperature of less than about 300° C. with the difference in melting point temperature of the organic compounds employed being not more than about 100° C.;

and wherein, upon combining said crystalline organic compounds with from 0–10% binder, from 0–5% lubricant and from 0–2% pigment, the resulting thermal cutoff composition is capable of withstanding a 240 volt, 60 Hz sinusoidal potential between electrical conductors at least 5° C. above the melt transition temperature for at least about one minute without conducting greater than 250 mA.

11. The thermal cutoff composition of claim 10 wherein said resulting composition is capable of withstanding a 240 volt, 60 Hz sinusoidal potential between electrical conductors at least 60° C. above the melt transition temperature for at last about one minute without conducting greater than 250 mA.

12. The thermal cutoff composition of claim 10 wherein said at least two organic compounds are selected from the group consisting of:

2H-1-benzopyran-2-one; n-butyl-4-hydroxybenzoate; phenylbenzoate; diphenylphthalate; 4-hydroxy-3-methoxybenzaldehyde; 1,3-diphenylbenzene; 1,4-dibromobenzene; triphenylmethane; 4,4'methylene bis (benzeneamine); diphenylethanedione; pentanedioic acid; n-propyl-4-hydroxybenzoate; xanthene; 3,5-dimethylpyrazole; 1,3-benzenediol; N-phenyl-2-napthylamine; N-phenylacetamide; 9H-fluorene; m-phenylenedibenzoate; dihydro-2,5-furandione; 2,5-pyrrolidinedione; 3-pyridinecarboxamide; phthalic anhydride; p-toluenesulfonamide; dimethyl terephthalate; N-(4-methylphenyl)acetamide; hexanedioic acid; N-phenylbenzamide; 4,4'-dibromobiphenyl; mannitol; 4-(1,1-dimethylethyl)benzoic acid; N-(2,6-dimethylphenyl)acetamide; 2,4-dinitrobenzeneamine; 7-hydroxy-4-methylcoumarin; 5,5-diethyl-2,4,6(IH,3H,5H)-pyrimidinetrione; 1,4-diphenylbenzene; ihositol; 6-phenyl-1,3,5-triazine-2,4-diamine; 3,7-dihydro-1,3,7-trimethyl-1H-purine-2,6-dione; 1,1'-bi-2-naphthol; 4-hydroxy-3-methoxybenzoic acid; 2,3-dimethylanthraquinone; 2-phenylindole; 2-methylphenylacetic acid; 2-phenylbenzimidazole; 1,3,5-trimethyl-2,4,6tris(3,5-di-tertbuttyl-4-hydroxybenzyl)benzene; hydantoin; 7-hydroxycoumarin; carbanilide; 1,5-dichloroanthraquinone; 1,1,1-tris(4-hydroxyphenyl) ethane; 1-aminoanthraquinone; 2,3,5,6-tetrabromo-p-xylene; 1,5-dihydroxynapthalene; 2-quinoxalinol; 2,4-diamino-6-methyl-1,3,5-triazine; 7-chloro-4-hydroxyquinoline; alizarin; anthraquinone; 2,4-diamino-6-hydroxypyrimidine; 2-phenylbenzimidazole; 2-amino-4-hydroxy-6-methylpyrimidine; 4-amino-2,6-dihydroxypyrimidine; 2-amino-4,6-dihydroxypyrimidine and uracil.

13. The thermal cutoff composition of claim 10 wherein a binder selected from the group consisting of polyethylene glycol, 1,3-benzenediol, epoxies, and polyamides is combined with the organic compounds.

14. The thermal cutoff composition of claim 10 wherein a lubricant selected from the group consisting of calcium stearate, boron nitride, magnesium silicate, and polytetrafluoroethylene is combined with the organic compounds.

15. The thermal cutoff composition of claim 10 wherein said composition is pelletized.

16. The thermal cutoff composition of claim 10 wherein said composition is non-deliquescent.

17. The thermal cutoff composition of claim 10 wherein said composition has a depressed melting point of at least 5° C.

18. A thermal cutoff composition shaped to provide an actuating function at a target melting point, comprising:
 a combination of at least two organic compounds, said compounds having a melting temperature of less than about 300° C., with the difference in melting point temperature of at least 2 organic compounds employed being not more than 100° C.;
 0–10% binder;
 0–5% lubricant; and
 0–2% pigment,
wherein the melting point of the thermal cutoff composition is the target melting point, and is less than that of any of the individual organic compounds.

19. A thermal cutoff composition according to claim 18, comprising a binder.

20. A thermal cutoff composition according to claim 18, comprising a lubricant.

21. A thermal cutoff composition according to claim 18, in the form of a pellet.

22. A thermal cutoff composition according to claim 18, wherein the melting point of the thermal cutoff composition is at least 5° C. less than the melting point of an individual organic compound.

23. A thermal cutoff composition according to claim 18, wherein the composition is capable of withstanding a 240 volt, 60 Hz sinusoidal potential between electrical conductors at least 5° C. above the melt transition temperature for at least 1 minute without conducting greater than 250 mA.

24. The thermal cutoff composition of claim 3 wherein said composition is capable of withstanding a 240 volt, 60 Hz sinusoidal potential between electrical conductors at least 10° C. above the melt transition temperature for at least about one minute without conducting greater than 250 mA.

25. The thermal cutoff composition of claim 1 comprising a lubricant selected from the group consisting of calcium stearate, boron nitride, magnesium silicate, and polytetrafluoroethylene.

26. The thermal cutoff composition of claim 10 wherein said resulting composition is capable of withstanding a 240 volt, 60 Hz sinusoidal potential between electrical conductors at least 10° C. above the melt transition temperature for at least about one minute without conducting greater than 250 mA.

\* \* \* \* \*

UNITED STATES PATENT AND TRADEMARK OFFICE
CERTIFICATE OF CORRECTION

| | | |
|---|---|---|
| PATENT NO. | : 6,673,257 B1 | |
| APPLICATION NO. | : 09/659981 | |
| DATED | : January 6, 2004 | |
| INVENTOR(S) | : Christine M. Hudson | |

It is certified that error appears in the above-identified patent and that said Letters Patent is hereby corrected as shown below:

Column 5,
Table I-Continued, line 27, under CAS Registry No., "1198-57-2" should be --1196-57-2--.

Columns 5-6,
Table II,
Line 2, 3$^{rd}$ Column, "91-78-9" should be --91-76-9--.
Line 2, 10$^{th}$ Column, "123-58-8" should be --123-56-8--.
Line 4, 1$^{st}$ Column, "91-78-9" should be --91-76-9--.
Line 9, 6$^{th}$ Column, "131.4(-2.8)" should be --131.4(-2.6)--.
Line 12, 1$^{st}$ Column, "120-81-6" should be --120-61-6--.
Line 12, 8$^{th}$ Column, "121.7 (-8.7)" should be --121.7 (-6.7)--.
Line 13, 1$^{st}$ Column, "123-58-8" should be --123-56-8-.
Line 14, 6$^{th}$ Column, "112.8(-9.6)" should be --112.6(-9.6)--.
Line 17, 7$^{th}$ Column, "97.8(-8.8)" should be --97.8(-6.6)--.
Line 19, 7$^{th}$ Column, "91.6(6.6)" should be --91.6(-6.6)--.
Line 20, 1$^{st}$ Column, "108-37-6" should be --106-37-6--.
Line 21, 10$^{th}$ Column, "64.9(-5)" should be --64.9(-6)--.

Columns 7-8,
Table II-Continued
Line 4, 1$^{st}$ Column, "91-78-9" should be --91-76-9--.
Line 10, 1$^{st}$ Column, "120-81-6" should be --120-61-6--.
Line 14, 3$^{rd}$ Column, "74.6(-5.8)" should be --74.6(-5.6)--.
Line 20, 3$^{rd}$ Column, "87.4(-8.7)" should be --67.4(-6.7)--.
Line 20, 5$^{th}$ Column, "59.7(-2.8)" should be --59.7(-2.6)--.
Line 20, 7$^{th}$ Column, "80.0(-5.4)" should be --60.0(-5.4)--.
Line 20, 8$^{th}$ Column, "56.1(-1.4)" should be --56.1(-4.4)--.

Column 9
Line 48, claim 5, "60°" should be --10°--.

UNITED STATES PATENT AND TRADEMARK OFFICE
CERTIFICATE OF CORRECTION

PATENT NO. : 6,673,257 B1
APPLICATION NO. : 09/659981
DATED : January 6, 2004
INVENTOR(S) : Christine M. Hudson It is certified that error appears in the above-identified patent and that said Letters Patent is hereby corrected as shown below:

Column 10,
Lines 35-36, claim 12, "ihositol" should be --inositol--.
Line 41, claim 12, "tertbuttyl" should be --tertbutyl--.

Signed and Sealed this

First Day of August, 2006

JON W. DUDAS
*Director of the United States Patent and Trademark Office*